United States Patent
Jameson

(10) Patent No.: US 7,060,867 B2
(45) Date of Patent: Jun. 13, 2006

(54) ABSORBENT ARTICLE WITH A BODY FACING LINER HAVING DISCRETELY PLACED LOTION DEPOSITS

(75) Inventor: Lee K. Jameson, Roswell, GA (US)

(73) Assignee: Kimberly-Clark Worldwide, Inc., Neenah, WI (US)

(*) Notice: Subject to any disclaimer, the term of this patent is extended or adjusted under 35 U.S.C. 154(b) by 540 days.

(21) Appl. No.: 10/305,779

(22) Filed: Nov. 27, 2002

(65) Prior Publication Data

US 2004/0102750 A1    May 27, 2004

(51) Int. Cl.
A61F 13/15    (2006.01)
A61F 13/00    (2006.01)

(52) U.S. Cl. ............. 604/364; 604/304; 604/385.01; 602/48; 424/443

(58) Field of Classification Search ........... 604/289, 604/304, 364, 385.01; 602/48; 424/402, 424/443, 445, 446, 447, 449
See application file for complete search history.

(56) References Cited

U.S. PATENT DOCUMENTS

| | | | |
|---|---|---|---|
| 3,489,148 A | | 1/1970 | Duncan et al. |
| 4,699,792 A | * | 10/1987 | Nick et al. ............ 424/446 |
| 4,711,781 A | * | 12/1987 | Nick et al. ............ 424/446 |
| 4,990,144 A | * | 2/1991 | Blott ..................... 604/304 |
| 5,431,643 A | | 7/1995 | Ouellette et al. |
| 5,505,720 A | * | 4/1996 | Walters et al. ........ 604/378 |
| 5,538,732 A | * | 7/1996 | Smith et al. .......... 424/402 |
| 5,843,056 A | | 12/1998 | Good et al. |
| 5,855,999 A | | 1/1999 | McCormack |
| 5,879,341 A | | 3/1999 | Odorzynski et al. |
| 5,990,377 A | * | 11/1999 | Chen et al. ........... 604/381 |
| 6,001,380 A | * | 12/1999 | Smith et al. .......... 424/402 |
| 6,149,934 A | | 11/2000 | Krzysik et al. |
| 6,166,285 A | | 12/2000 | Schulte et al. |
| 6,261,593 B1 | * | 7/2001 | Muchin et al. ....... 424/443 |
| 6,281,407 B1 | | 8/2001 | Warner et al. |
| 6,287,581 B1 | | 9/2001 | Krzysik et al. |
| 6,296,862 B1 | | 10/2001 | Paul et al. |
| 6,656,168 B1 | * | 12/2003 | Braverman et al. ... 604/308 |
| 2001/0025162 A1 | | 9/2001 | Roe et al. |

(Continued)

FOREIGN PATENT DOCUMENTS

DE    3830056 A1    3/1990

(Continued)

OTHER PUBLICATIONS

U.S. Appl. No. 10/022,810, filed Dec. 18, 2001, Braverman et al.

(Continued)

Primary Examiner—Tatyana Zalukaeva
Assistant Examiner—Michael G. Bogart
(74) Attorney, Agent, or Firm—Dority & Manning

(57) ABSTRACT

An absorbent article includes an outer cover member, a liner, and an absorbent body structure disposed between the cover member and the liner. A first matrix of discrete deposits of a skin wellness lotion formulation are applied relative to the body facing surface of the liner so as to contact the wearer's skin. The lotion formulation deposits have a phase-change temperature less than body temperature. A second matrix of discrete deposits of a phase-change liquid are applied to the body facing surface of the liner interspaced with the lotion deposits. These phase-change liquid deposits have a phase-change temperature greater than body temperature. The phase-change lotion deposits have a height above the body facing surface greater than the height of the phase-change liquid deposits.

32 Claims, 4 Drawing Sheets

U.S. PATENT DOCUMENTS

| | | |
|---|---|---|
| 2001/0031938 A1 | 10/2001 | DeLucia et al. |
| 2002/0087129 A1* | 7/2002 | Di Luccio et al. .......... 604/304 |
| 2002/0138054 A1 | 9/2002 | Erdman et al. |
| 2003/0106605 A1* | 6/2003 | Jameson et al. .............. 141/98 |
| 2003/0203015 A1* | 10/2003 | Aledo et al. ................ 424/445 |
| 2004/0099392 A1* | 5/2004 | Liu et al. .................... 162/184 |

FOREIGN PATENT DOCUMENTS

| | | |
|---|---|---|
| DE | 4437165 A1 | 4/1996 |
| EP | 0747029 A1 | 12/1996 |

OTHER PUBLICATIONS

EPO Search Report, Mar. 23, 2004.

* cited by examiner

ABSORBENT ARTICLE WITH A BODY FACING LINER HAVING DISCRETELY PLACED LOTION DEPOSITS

TECHNICAL FIELD OF THE INVENTION

The present invention relates generally to the field of absorbent articles and garments, such as children's training pants, disposable diapers, incontinence articles, and the like, and more particularly to an improved lotionized liner for use with such articles.

BACKGROUND

Conventional absorbent articles, such as disposable diapers, employ absorbent materials located between a liquid pervious bodyside liner and a liquid impermeable outer cover to absorb body exudates. Typically, the liquid pervious bodyside liners have been constructed of nonwoven materials such as spunbond polyolefin materials. Unfortunately, such materials do not always provide a soft, nonabrasive contact with the skin. In particular, during continuous use of absorbent articles containing such liners, the wearer's skin can become quite irritated and red, particularly in the presence of urine and feces. The abrasion resulting from such liners and the presence of urine and feces can undesirably lead to the onset of diaper dermatitis (diaper rash). Diaper dermatitis can afflict almost every infant at some time during the diaper wearing years. Although other factors influence the onset of diaper dermatitis, critical factors include the abrasiveness of the bodyside liner and the hydration level of the wearers skin.

To prevent body exudates from contacting the wearer's skin, the caregiver often applies skin protective products directly to the skin of the wearer before positioning the article on the wearer. Such products have included petrolatum, mineral oil, talc, corn starch, or various other commercially available rash creams or lotions. This procedure typically involves the caregiver applying the product to their hand and then transferring the product to the wearer's skin.

To eliminate the caregiver from contacting the products and to reduce skin abrasion and improve skin health, attention has been given in the art to providing lotion formulations directly on the bodyside liners such that, in use, the lotion formulation either transfers to the skin or provides lubricity thereby reducing the friction between the liner and the skin. Reference is made, for example, to U.S. Pat. Nos. 6,149,934; 6,287,581; and 6,296,862, such references incorporated herein by reference for all purposes.

With conventional lotion applications, relatively large amounts of the lotion are incorporated on the liner to ensure sufficient transfer of the lotion to the wearer's skin to deliver the desired skin benefit. This is due primarily to the fact that the lotion tends to migrate away from the surface of the liner and into the liner and underlying absorbent structure leaving less on the surface to transfer to the skin. This migration problem is particularly evident at higher temperatures such as those at the skin surface in use. Thus, to ensure adequate surface coverage, it has been a practice to coat the bodyside liners in large areas or bands. However, this practice may inhibit the ability to intake liquids through the liner. Also, to ensure transfer to the wearer's skin, it is necessary for the entire coated area to contact the skin. This condition may lead to increased abrasion.

The present invention provides an improved lotionized bodyside liner configuration.

SUMMARY

Objects and advantages of the invention will be set forth in part in the following description, or may be obvious from the description, or may be learned through practice of the invention.

In general, the present invention relates to a unique lotionized bodyside liner configuration for use in a variety of absorbent articles, such as disposable diapers, child's training pants, incontinence articles, diaper pants, disposable swim pants, and the like. For purposes of description only, embodiments of an absorbent article according to the invention will be made with reference herein to a disposable diaper. It should, however, be appreciated that the invention is not limited to disposable diapers and may be used in other absorbent articles.

An absorbent article according to the invention includes an outer cover member and an inner liner member. An absorbent body structure is disposed between the outer cover member and the liner. The liner defines a body facing surface that, in use of the article, is disposed directly adjacent to the wearer's skin.

The absorbent article includes a pattern or matrix of discrete deposits of a phase-change liquid applied to the body facing surface of the liner. The phase-change liquid deposits have a height with respect to the body facing surface of the liner so as to maintain the body facing surface displaced from the wearer's skin in use of the article. The phase-change liquid deposits may be, for example, a wax, thermoplastic, adhesive, or any other skin-friendly substance that can be applied in a liquid or molten state to the body facing surface of the liner and subsequently solidifies into discrete deposits. The phase-change liquid deposits have a melting temperature greater than body temperature so that the deposits maintain their integrity in use of the article.

A pattern or matrix of discrete deposits of a phase-change skin wellness lotion formulation are applied relative to the body facing surface of the liner so as to extend above the phase-change liquid deposits. The phase-change lotion deposits have a phase-change temperature that is less than body temperature. Thus, in use of the article, the phase-change lotion deposits contact the wearer's skin and, due to body heat, transfer the lotion formulation to the wearer's skin. Once the phase-change lotion deposits are sufficiently depleted, the phase-change liquid deposits will come into contact with the wearer's skin and will maintain the liner away from the skin during further use of the article.

In a particular embodiment of the invention, the skin wellness lotion deposits are applied directly to the body facing surface of the liner as discrete deposits interspaced with the phase-change liquid deposits. For example, the lotion deposits and phase-change liquid deposits may be defined as discrete droplets that have solidified into dome-like structures on the body facing surface. The dome-like structures may have a radius of between about 0.005 mm and about 3.0 mm. The structures may have a height above the body facing surface that is about equal to their radius. For embodiments wherein the skin wellness lotion deposits are separately applied as discrete deposits to the body facing surface of the liner, it may be desired that the lotion deposits have a height with respect to the body facing surface that is greater than the height of the phase-change liquid deposits. Alternately, the two types of deposits may have the same height. Desirably, the skin wellness lotion deposits should not have a height that is less than the height of the phase-change liquid deposits.

In one embodiment of the article according to the invention, the deposits of the skin wellness lotion and the phase-change liquid are applied in a generally uniform pattern over the entire body facing surface of the liner. In an alternate embodiment, the deposits are applied to discrete areas of the body facing surface. For example, the discrete areas may be specifically targeted with the skin wellness lotion deposits to treat particular skin conditions or to provide protection to particular skin areas. Likewise, the phase-change liquid deposits may be applied to targeted areas of the body facing surface of the liner to prevent abrasion of the liner against the wearer's skin only in particular regions of the article.

In one embodiment, the lotion deposits and phase-change liquid deposits are applied as a matrix of relatively thin alternating lines. The lines may be continuous. In an alternate embodiment, the deposits may be defined as broken lines, for example, lines of discrete droplets that form into dome-like structures. The deposits may be applied to the body facing surface by any suitable method, particularly inkjet printing techniques, piezo-driven print head techniques, and so forth.

The skin wellness lotion formulation may comprise any combination of emollient, wax, and additional skin wellness agent, such as a medicant, ointment, moisturizer, and so forth. In a particular embodiment, the lotion formulation comprises a combination of a wax having a melting temperature below that of body temperature, an emollient, and a viscosity enhancer. The emollient may be an oil, ester, glycerol ester, ether, alkoxylated carbicsilic acid, alkoxylated alcohol, fatty alcohol, or mixtures thereof. In a particular embodiment, the emollient is a petroleum based emollient, such as a petrolatum.

The phase-change liquid may be a wax, petroleum based product, thermoplastic, adhesive, or combinations thereof. The phase-change liquid generally serves the purpose of defining a raised topography to maintain the body facing surface of the liner away from the wearer's skin. The phase-change liquid may be any application or composition which is capable of adhering or being applied to the liner so that, upon solidification, discrete barrier topographies are defined on the liner. The phase-change liquid should be a skin-friendly composition.

In a particular embodiment, the phase-change liquid may be a wax having a melting point greater than body temperature.

In still another embodiment, the skin wellness lotion deposits may be applied directly on top of the phase-change liquid deposits. With this embodiment, upon use of the article, the lotion deposits will first contact the wearer's skin and will transfer the skin wellness formulation to the skin. Once the lotion deposits have been depleted, the phase-change liquid deposits are exposed and will subsequently come into contact with the wearer's skin and maintain the liner material displaced from the skin.

Aspects of the invention will be described below in greater detail by reference to particular embodiments, examples of which are illustrated in the figures.

BRIEF DESCRIPTION OF THE FIGURES

A full and enabling disclosure of the present invention, including the best mode thereof, directed to one of ordinary skill in the art, is set forth more particularly in the remainder of the specification, which makes reference to the appended figures in which.

DETAILED DESCRIPTION

Figure 1:
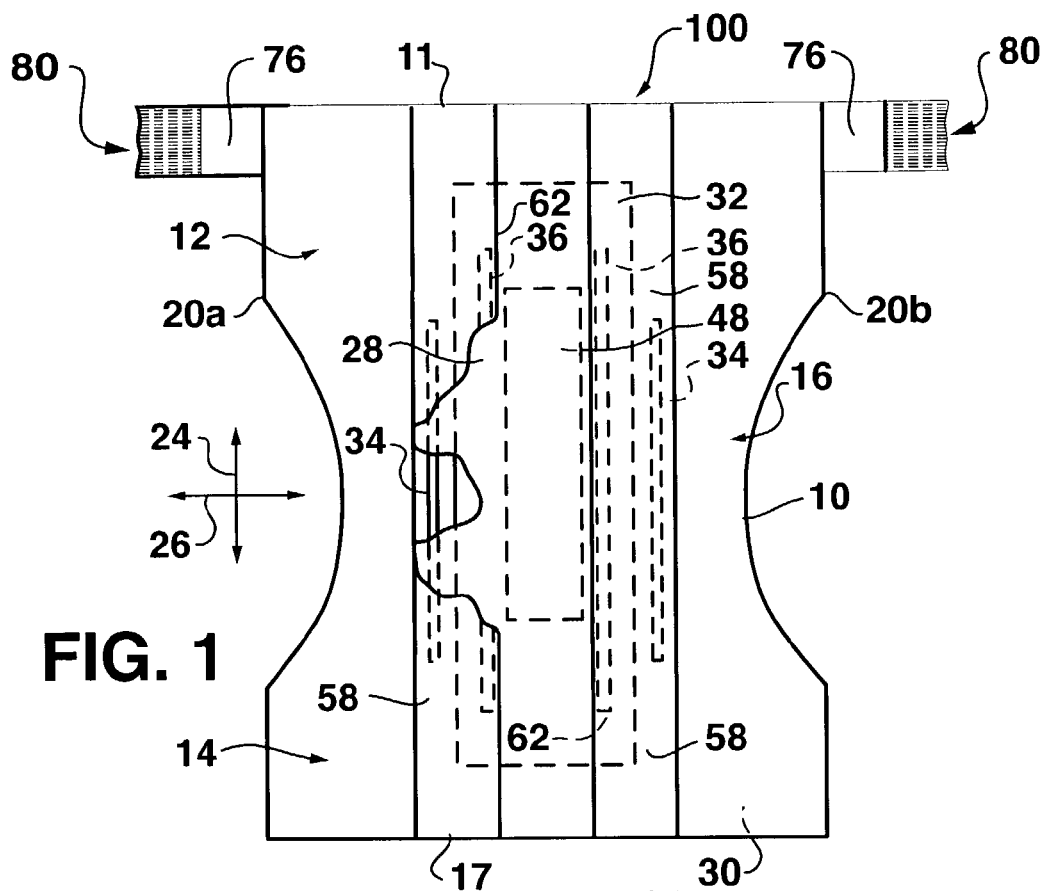
FIG. 1 is a body side plan view of an absorbent article, in particular a disposable diaper, according to the invention with all elastic member shown in an extended stretched condition.

The invention will now be described in detail with reference to particular embodiments thereof. The embodiments are provided by way of explanation of the invention, and are not meant as a limitation of the invention. For example, features described or illustrated as part of one embodiment may be used with another embodiment to yield still a further embodiment. It is intended that the present invention include these and other modifications and variations as come within the scope and spirit of the invention.

Within the context of the present description, the following terms may have the following meanings:

"Attached" and "joined" refers to the bonding, adhering, connecting, and any other method for attaching or joining two elements. Two elements will be considered to be attached or joined together when they are bonded directly to one another or indirectly to one another, such as when each is directly attached to an intermediate element.

"Extendable" means that property of a material or composite by virtue of which it stretches or extends in the direction of an applied biasing force normally exerted by a consumer by at least about 25% of its relaxed length. An extendable material may or may not have recovery properties. For example, an elastomeric material is an extendable material having recovery properties. A meltblown web may be extendable, but not have recovery properties.

"Elastomeric", "elastic," and "elasticized" refer to a material or composite which can be elongated by at least 25% of its relaxed length and which will recover, upon release of the applied force, at least 10% of its elongation. It is generally preferred that the elastomeric material or composite be capable of being elongated by at least 100%, more preferably by at least 300%, of it relaxed length and recover at least 50% of its elongation. An elastomeric material is an extendable material having recovery properties.

"Neck-bonded" laminate refers to a composite material having an elastic member that is bonded to a non-extensible member while the non-elastomeric member is extended in the machine direction creating a necked material that is elastic in the cross-direction. Examples of neck-bonded laminates are disclosed in U.S. Pat. Nos. 4,965,122; 4,981,747; 5,226,992; and 5,336,545, which are incorporated herein by reference in their entirety for all purposes.

"Reversibly-necked material" refers to a necked material that has been treated while necked to impart memory to the material so that when force is applied to extend the material to it pre-necked dimensions, the necked and treated portions will generally recover to their necked dimensions upon termination of the force. A reversibly-necked material may include more than one layer. For example, multiple layers of spunbonded web, multiple layers of meltblown web, multiple layers of bonded carded web or any other suitable combination of mixtures thereof. The production of reversibly-necked materials is described in U.S. Pat. Nos. 4,965,122 and 4,981,747, incorporated herein by reference for all purposes.

"Stretch-bonded" laminate refers to a composite material having at least two layers in which one layer is a gatherable layer and the other layer is an elastic layer. The layers are joined together when the elastic layer is in an extended condition so that upon relaxing the layers, the gatherable layer is gathered. For example, one elastic member can be bonded to another member while the elastic member is extended at least about 25% of its relaxed length. Such a multilayer composite elastic material may be stretched until the non-extensible layer is fully extended. Examples of stretch-bonded laminates are disclosed, for example, in U.S. Pat. Nos. 4,720,415, 4,789,699, 4,781,966, 4,657,802, and 4,655,760, which are incorporated herein by reference in their entirety for all purposes.

"Neck stretch-bonded" laminate refers a laminate made from the combination of a neck-bonded laminate and a stretch-bonded laminate. Examples of necked stretch bonded laminates are disclosed in U.S. Pat. Nos. 5,114,781 and 5,116,662, which are incorporated herein in their entirety by reference thereto for all purposes. Of particular advantage, a necked stretch bonded laminate can be stretchable in both the machine and cross-machine directions.

"Nonwoven web" refers a web that has a structure of individual fibers or threads which are interlaid, but not in an identifiable, repeating manner. Nonwoven webs may be formed, for example, by a variety of processes including melt-blowing, spunbonding, and bonded carded web processes.

"Sheet" refers to a layer which may be either a film or a nonwoven web.

"Member" when used in the singular can refer to a single element or a plurality of elements.

"Phase-change" refers to a material which is processed in a liquid or molten state and then solidifies or returns to its natural state when cooled.

"Viscosity" refers to the viscosity in centipoise determined according to ASTM D3236, entitled "Standard Test Method for Apparent Viscosity of Hot Melt Adhesives and Coating Materials."

"Melting point" refers to the temperature at which the majority of the melting occurs, it being recognized that melting actually occurs over a range of temperatures.

Aspects of the invention are explained below by reference to embodiments of a disposable diaper. As mentioned, the invention is not limited to diapers, and as utility for various other absorbent articles, including, training pants, swim pants, incontinence articles, and the like.

FIG. 1 shows a body facing plan view of a representative article 100, in this case a disposable diaper, in its generally flat-out, uncontracted state (i.e., with substantially all elastic induced gathering and contraction removed). The article components are attached or joined together by conventional suitable attachment methods such as adhesive bonds, sonic bonds, thermal bonds, pinning, stitching or any other attachment technique known in the art, as well as combinations thereof. For example, a uniform continuous layer of adhesive, a patterned layer of adhesive, a sprayed pattern of adhesive or an array of separate lines, swirls or spots of construction adhesive may be used to affix the various components.

With reference to FIG. 1 in general, the representatively shown diaper 100, is illustrated. This diaper 100 is similar in many aspects to the Huggies® brand of disposable diapers from Kimberly-Clark Corporation of Neenah, Wis., USA. The article 100 includes a body or chassis 10 having lateral sides 20a and 20b, a lengthwise, longitudinal direction 24, a lateral, transverse cross-direction 26, a front waist region 14, a back waist region 12, and an intermediate crotch region 16 interconnecting the front and back waist regions. The waist regions 12 and 14 comprise those portions of the article 100 which when worn, wholly or partially cover or encircle the waist or mid-lower torso of the wearer. The front 14 and back 12 waist regions have front and back waistband portions 17, 11. The intermediate crotch region 16 lies between and interconnects the waist regions 14 and 12, and comprises that portion of the article 100 which, when worn, is positioned between the legs of the wearer and covers the lower torso of the wearer. Thus, the intermediate crotch region 16 is an area where repeated fluid surges typically occur in the training pant or other disposable absorbent article.

The diaper 100 will typically include a porous, liquid permeable bodyside liner 28 overlying an absorbent body structure 32, and a substantially liquid impermeable outer cover member 30. The absorbent body structure 32 is positioned and attached between the outer cover member 30 and bodyside liner 28. In certain embodiments, a surge layer 48 may be optionally located adjacent the absorbent structure and attached, for example, by way of an adhesive.

The outer cover member 30 and bodyside liner 28 may be separate sheets joined at the respective lateral sides 20a and 20b. Leg elastics 34 may be incorporated along the lateral side margins of the chassis 10 outboard of the absorbent body structure 32 and are configured to draw and hold the chassis 10 against the legs of the wearer. The elastic members 34 are secured to the chassis 10 in an elastically contracted state so that in a normal under-strain condition, the elastic members 34 effectively contract against the chassis. The use of elastic leg members in absorbent articles such as disposable diapers and training pants is widely known and understood in the art.

Attachment tabs 76 may be provided for securing the article 100 to a wearer. The tabs 76 may be elastomeric and incorporate any manner of conventional fastening device 80 for this purpose. For example, in the illustrated embodiment, the fastening device 80 is defined by conventional microhook material that attaches to a nonwoven material (not shown) provided on the outside of the front region, as is commonly understood in the art. The fastening device 80 may also be a releasable adhesive, mechanical fastener, and so forth.

Various materials are available and known in the art for use as the outer cover member 30. Constructions of the outer cover member 30 may comprise a woven or non-woven fibrous web layer which has been totally or partially constructed or treated to impart the desired levels of liquid impermeability to selected regions that are adjacent or proximate the absorbent body. Alternatively, a separate liquid impermeable material could be associated With the absorbent body structure 32. The outer cover may include a gas-permeable, nonwoven fabric layer laminated to a polymer film layer which may or may not be gas-permeable. Other examples of fibrous, cloth-like outer cover materials can comprise a stretch thinned or stretch thermal laminate material. Although the outer cover member 30 typically provides the outermost layer of the article, optionally the article may include a separate outer cover component member which is additional to the outer cover member.

The outer cover member 30 may be formed substantially from an elastomeric material. Alternately, the outer cover member may be formed from a non-elastomeric and non-extendable material. The outer cover member 30 may, for example, be composed of a single layer, multiple layers, laminates, spunbond fabrics, films, meltblown fabrics, elastic netting, microporous web, bonded carded webs or foams comprised of elastomeric or polymeric materials. Elastomeric nonwoven laminate webs may include a nonwoven material joined to one or more gatherable nonwoven webs, films, or foams. Stretch bonded laminates (SBL), neck bonded laminates (NBL), and necked stretch bonded Laminates (NSBL) are examples of elastomeric composites. Nonwoven fabrics are any web of material which has been formed without the use of textile weaving processes which produce a structure of individual fibers which are interwoven in an identifiable repeating manner. Examples of suitable materials are spunbond-meltblown fabrics, spunbond-meltblown-spunbond fabrics, spunbond fabrics, or laminates of such fabrics with films, foams, or other nonwoven webs. Elastomeric materials may include cast or blown films, foams, or meltblown fabrics composed of polyethylene, polypropylene, or polyolefin copolymers, as well as combinations thereof. The outer cover 30 may include materials that have elastomeric or extensible properties obtained through a mechanical process, printing process, heating process, or chemical treatment. For examples such materials may be apertured, creped, neck-stretched, heat activated, embossed, and micro-strained; and may be in the form of films, webs, and laminates.

The bodyside liner 28 may be formed from any one or combination of suitable materials known in the art. Various woven and nonwoven fabrics can be used as the liner 28. For example, the material may include a meltblown web, a spunbonded web, or a bonded-carded-web composed of synthetic continuous or discrete polymer fibers and/or natural fibers, a pattern bonded spunbonded web, airlaid web, or bonded carded web, as well as combinations thereof. The various fabrics can be composed of natural fibers, synthetic fibers or combinations thereof. In particular aspects, the material may be comprised of polymer fibers, networks, laminates, liquid permeable films, cellulosic fibers, rayon, water swellable gels, as well as combinations thereof. Suitable polymers can include polypropylene, polyethylene, polyester, and bicomponent materials composed of these polyolefins.

The liner 28 may be composed of a substantially hydrophobic material, and the hydrophobic material may optionally be treated with a surfactant or otherwise processed to impart a desired level of wettability and hydrophilicity. In a particular embodiment of the invention, the material can be a nonwoven, spunbond polypropylene fabric. The fabric can be surface treated with an operative amount of surfactant, such as about 0.6% AHCOVEL Base N62 surfactant, available from ICI Americas, a business having offices located in Wilmington, Del. The surfactant can be applied by any conventional means, such as spraying, dipping, printing, brush coating or the like. The fibers forming the nonwoven material may be mono-component, bi-component, or multi-component fibers, and combinations thereof.

The liner 28 may include blends or laminates of fibers, scrim, webs, and films with perforations, apertures, creping, heat activation, embossing, micro-straining, chemical treatment, or the like, as well as combinations thereof.

The article 100 may incorporate separate containment flaps 58 attached to the chassis 10 at the waistband portions 11, 17 and along a longitudinal side thereof outboard of the absorbent structure 32. The flaps 58 may contain elastic members 36 along at least a portion of their free laterally inward side 62. The construction of such containment flaps 58 is well known and need not be described in detail. Suitable constructions and arrangements for the containment flaps 58 are described, for example, in U.S. Pat. No. 4,704,116, which is incorporated herein by reference for all purposes.

The absorbent body structure 32 can be any structure or combination of components which are generally compressible, conformable, non-irritating to a wearer's skin, and capable of absorbing and retaining liquids and certain body wastes. For example, the structure 32 may include an absorbent web material of cellulosic fibers (e.g., wood pulp fibers), other natural fibers, synthetic fibers, woven or nonwoven sheets, scrim netting or other stabilizing structures, superabsorbent material, binder materials, surfactants, selected hydrophobic materials, pigments, lotions, odor control agents or the like, as well as combinations thereof. In a particular embodiment, the absorbent web material is a matrix of cellulosic fluff and superabsorbent hydrogel-forming particles. The cellulosic fluff may comprise a blend of wood pulp fluff. One preferred type of fluff is identified with the trade designation CR 1654, available from U.S. Alliance of Childersburg, Ala., USA, and is a bleached, highly absorbent wood pulp containing primarily soft wood fibers. The absorbent materials may be formed into a web structure by employing various conventional methods and techniques. For example, the absorbent web may be formed with a dry-forming technique, an air forming technique, a wet-forming technique, a foam-forming technique, or the like, as well as combinations thereof. Methods and apparatus for carrying out such techniques are well known in the art.

As a general rule, the superabsorbent material is present in the absorbent web in an amount of from about 0 to about 90 weight percent based on total weight of the web. The web may have a density within the range of about 0.10 to about 0.35 grams per cubic centimeter.

Superabsorbent materials are well known in the art and can be selected from natural, synthetic, and modified natural polymers and materials. The superabsorbent materials can be inorganic materials, such as silica gels, or organic compounds, such as crosslinked polymers. Typically, a superabsorbent material is capable of absorbing at least about 15 times its weight in liquid, and desirably is capable of absorbing more than about 25 times its weight in liquid. Suitable superabsorbent materials are readily available from various suppliers. For example, Favor 880 superabsorbent is available from Stockhausen GmbH of Germany; and Drytech 2035 is available from Dow Chemical Company, of Midland Mich., USA.

After being formed or cut into a desired shape, the absorbent web material may be wrapped or encompassed by a suitable wrap that aids in maintaining the integrity and shape of the absorbent structure 32.

The absorbent web material may also be a coform material. The term "coform material" generally refers to composite materials comprising a mixture or stabilized matrix of thermoplastic fibers and a second non-thermoplastic material. As an example, coform materials may be made by a process in which at least one meltblown die head is arranged near a chute through which other materials are added to the web while it is forming. Such other materials may include, but are not limited to, fibrous organic materials such as woody or non-woody pulp such as cotton, rayon, recycled paper, pulp fluff and also superabsorbent particles, inorganic absorbent materials, treated polymeric staple fibers and the like. Any of a variety of synthetic polymers may be utilized as the melt-spun component of the coform material. For instance, in some embodiments, thermoplastic polymers can be utilized. Some examples of suitable thermoplastics that can be utilized include polyolefins, such as polyethylene, polypropylene, polybutylene and the like; polyamides; and polyesters. In one embodiment, the thermoplastic polymer is polypropylene. Some examples of such coform materials are disclosed in U.S. Pat. No. 4,100,324 to Anderson, et al.; U.S. Pat. No. 5,284,703 to Everhart, et al.; and U.S. Pat. No. 5,350,624 to Georger, et al.; which are incorporated herein in their entirety by reference thereto for all purposes.

The absorbent body structure 32 may include an elastomeric coform absorbent web material, for example as described in U.S. Pat. Nos. 4,663,220 and 4,741,949. In particular aspects, the elastomeric coform material can have an overall coform basis weight which is at least a minimum of about 50 g/m$^2$. The coform basis weight can alternatively be at least about 100 g/m$^2$ and can optionally be at least about 200 g/m$^2$ to provide improved performance. In addition, the coform basis weight can be not more than about 1200 g/m$^2$. Alternatively, the coform basis weight can be not more than about 900 g/m$^2$, and optionally, can be not more than about 800 g/m$^2$ to provide improved benefits. These values are important because they can provide the absorbent body structure with desired stretchability and structural stability without excessively degrading the physical properties or the liquid-management functionalities of the absorbent body structure. Retention portions having excessively low proportions of elastomeric coform material may not be sufficiently stretchable. An absorbent web material having excessively large amounts of elastomeric coform materials can exhibit an excessive degradation of their absorbency functionalities, such as an excessive degradation of intake, distribution and/or retention properties.

Other examples of elastomeric absorbent structures are described in U.S. Pat. No. 6,362,389 B1, incorporated herein by reference for all purposes.

The absorbent web material utilized in the absorbent body structure 32 is also selected so that the individual absorbent body structure possesses a particular individual total absorbency depending on the intended article of use. For example, for infant care products, the total absorbency can be within the range of about 200–900 grams of 0.9 wt % saline, and can typically be about 500 g of saline. For adult care products, the total absorbency can be within the range of about 400–2000 grams of saline, and can typically be about 1300 g of saline. For feminine care products, the total absorbency can be within the range of about 7–50 grams of menstrual fluid, and can typically be within the range of about 30–40 g of menstrual fluid.

As described, the absorbent body structure 32 may also include a surge management layer 48 which helps to decelerate and diffuse surges or gushes of liquid that may be rapidly introduced into the absorbent body of the article. Desirably, the surge management layer can rapidly accept and temporarily hold the liquid prior to releasing the liquid into the storage or retention portions of the absorbent structure. The surge layer can be located below the bodyside liner layer 28. Alternatively, the surge layer may be located on the body facing surface of the bodyside liner 28. Examples of suitable surge management layers are described in U.S. Pat. Nos. 5,486,166; and 5,490,846. Other suitable surge management materials are described in U.S. Pat. No. 5,820,973. The entire disclosures of these patents are hereby incorporated by reference in their entirety for all purposes.

As discussed, the article 100 includes discrete deposits of a skin wellness lotion formulation applied relative to the liner 28 so as to contact the wearer's skin and transfer the lotion formulation directly to the skin. The lotion formulation is a phase-change substance that is applied to the liner 28 in a liquid or partially liquid state, and subsequently solidifies into the discrete deposits. The solidified lotion deposits have a melt point generally at or below body temperature so that upon contacting the wearer's skin, the deposits melt and the lotion is transferred to the skin. The make-up of the lotion formulation is not a limiting feature of the invention and may include, for example, any combination of an emollient, a wax and, optionally, a viscosity enhancer. For example, the lotion formulation may include from about 5 to about 95 weight percent of an emollient, from about 5 to about 95 weight percent of a wax, and from about 1 to about 25 weight percent of a viscosity enhancer based on a total weight of the lotion formulation. The lotion formulation may include other ingredients as well.

The emollients act as lubricants to reduce the abrasiveness of the bodyside liner 28 to the skin and, upon transfer to the skin, help to maintain the soft, smooth and pliable appearance of the skin. Suitable emollients which can be incorporated into the lotion formulation include oils such as petroleum based oils, vegetable based oils, mineral oils, natural or synthetic oils, silicone oils, lanolin and lanolin derivatives, kaolin and kaolin derivatives and the like and mixtures thereof; esters such as cetyl palmitate, stearyl palmitate, cetyl stearate, isopropyl laurate, isopropyl myristate, isopropyl palmitate and the like and mixtures thereof; glycerol esters; ethers such as eucalyptol, cetearyl glucoside, dimethyl isosorbicide polyglyceryl-3 cetyl ether, polyglyceryl-3 decyltetradecanol, propylene glycol myristyl ether and the like and mixtures thereof; alkoxylated carboxylic acids; alkoxylated alcohols; fatty alcohols such as octyidodecanol, lauryl, myristyl, cetyl, stearyl and behenyl alcohol and the like and mixtures thereof; and the like and mixtures thereof. For example, a particularly well suited emollient is petrolatum. Other conventional emollients may also be added in a manner which maintains the desired properties of the lotion formulations set forth herein.

To provide the improved stability and transfer to the skin of the wearer, the lotion formulation may include from about 5 to about 95 weight percent, desirably from about 20 to about 75 weight percent, and more desirably from about 40 to about 60 weight percent of the emollient. Lotion formulations which include an amount of emollient greater than the recited amounts tend to have lower viscosities which undesirably leads to migration of the lotion. Whereas, lotion formulations which include an amount of emollient less than the recited amounts tend to provide less transfer to the wearer's skin.

The wax in the lotion formulations of the present invention primarily functions as an immobilizing agent for the emollient and any active ingredient. In addition to immobilizing the emollient and reducing it's tendency to migrate, the wax in the lotion formulation provides a tackiness to the lotion formulation which improves the transfer to the skin of the wearer. The presence of the wax also modifies the mode of transfer in that the lotion tends to fracture or flake off instead of actually rubbing off onto the skin of the wearer which can lead to improved transfer to the skin. The wax may further function as an emollient, occlusive agent, moisturizer, barrier enhancer and combinations thereof.

Suitable waxes which can be incorporated into the lotion formulation include animal, vegetable, mineral or silicone based waxes which may be natural or synthetic such as, for example, bayberry wax, beeswax, C30 alkyl dimethicone, candelilla wax, carnauba, ceresin, cetyl esters, esparto, hydrogenated cottonseed oil, hydrogenated jojoba oil, hydrogenated jojoba wax, hydrogenated microcrystalline wax, hydrogenated rice bran wax, japan wax, jojoba buffer, jojoba esters, jojoba wax, lanolin wax, microcrystalline wax, mink wax, motan acid wax, motan wax, ouricury wax, ozokerite, paraffin, PEG-6 beeswax, PEG-8 beeswax, rezowax, rice bran wax, shellac wax, spent grain wax, spermaceti wax, steryl dimethicone, synthetic beeswax, synthetic candelilla wax, synthetic carnuba wax, synthetic japan wax, synthetic jojoba wax, synthetic wax, and the like and mixtures thereof. For example, a particularly well suited wax includes about 70 weight percent ceresin wax, about 10 weight percent microcrystalline wax, about 10 weight percent paraffin wax and about 10 weight percent cetyl esters (synthetic spermaceti wax).

To provide the improved transfer to the skin of the wearer, the lotion formulation may include from about 5 to about 95 weight percent, desirably from about 25 to about 75 weight percent, and more desirably from about 40 to about 60 weight percent of the wax. Lotion formulations which include an amount of wax less than the recited amounts tend to have lower viscosities which undesirably leads to migration of the lotion. Whereas, lotion formulations which include an amount of wax greater than the recited amounts tend to provide less transfer to the wearer's skin.

A viscosity enhancer may be added to the lotion formulation to increase the viscosity to help stabilize the formulation on the bodyfacing surface the liner 28 and thereby reduce migration and improve transfer to the skin. Desirably, the viscosity enhancer increases the viscosity of the lotion formulation by at least about 50 percent, more desirably at least about 100 percent, even more desirably by at least about 500 percent, yet even more desirably by at least about 1000 percent, and even more desirably by at least about 5000 percent. Suitable viscosity enhancers which can be incorporated into the lotion formulation include polyolefin resins, lipophilic/oil thickeners, ethylene/vinyl acetate copolymers, polyethylene, silica, talc, colloidal silicone dioxide, zinc stearate, cetyl hydroxy ethyl cellulose and other modified celluloses and the like and mixtures thereof. For example, a particularly well suited viscosity enhancer is an ethylene/vinyl acetate copolymer commercially available from E. I. Dupont De Ne Mours, a business having offices located in Wilmington, Del. under the trade designation ELVAX.

To provide the improved transfer to the skin of the wearer, the lotion formulation may include from about 0.1 to about 25 weight percent, desirably from about 5 to about 20 weight percent, and more desirably from about 10 to about 15 weight percent of the viscosity enhancer for reduced migration and improved transfer to the wearer's skin.

If it is desired that the lotion formulation treat the skin, it can also include an active ingredient such as a diaper rash skin protectant. Skin protectants are a drug product which protects injured or exposed skin or mucous membrane surface from harmful or annoying stimuli. Suitable active ingredients, in addition to those mentioned above as suitable emollients, which can be incorporated into the lotion formulation include, but are not limited to, alantoin and its derivatives, aluminum hydroxide gel, calamine, cocoa butter, dimethicone, cod liver oil, glycerin, kaolin and its derivatives, lanolin and its derivatives, mineral oil, shark liver oil, talc, topical starch, zinc acetate, zinc carbonate, and zinc oxide and the like, and mixtures thereof. The lotion formulation may include from about 0.10 to about 95 weight percent of the active ingredient depending upon the skin protectant and the amount desired to be transferred to the skin.

In order to better enhance the benefits to the wearer, additional ingredients can be included in the lotion formulations of the present invention. For example, the classes of ingredients that may be used and their corresponding benefits include, without limitation: antifoaming agents (to reduce the tendency of foaming during processing); antimicrobial actives; antifungal actives; antiseptic actives; antioxidants (to improve product integrity); astringents—cosmetic (to induce a tightening or tingling sensation on skin); astringent—drug (a drug product which checks oozing, discharge, or bleeding when applied to skin or mucous membrane and works by coagulating protein); biological additives (to enhance the performance or consumer appeal of the product); colorants (to impart color to the product); deodorants (to reduce or eliminate unpleasant odor and protect against the formation of malodor on body surfaces); other emollients (to help to maintain the soft, smooth, and pliable appearance of the skin by their ability to remain on the skin surface or in the stratum corneum to act as lubricants, to reduce flaking, and to improve the skin's appearance); external analgesics (a topically applied drug that has a topical analgesic, anesthetic, or antpruritic effect by depressing cutaneous sensory receptors, of that has a topical counterirritant effect by stimulating cutaneous sensory receptors); film formers (to hold active ingredients on the skin by producing a continuous film on skin upon drying); fragrances (for consumer appeal), silicones/organomodified silicones (protection, tissue water resistance, lubricity, tissue softness), oils (mineral, vegetable, and animal); natural moisturizing agents (NMF) and other skin moisturizing ingredients known in the art; opacifiers (to reduce the clarity or transparent appearance of the product); powders (enhance lubricity, oil adsorption, provide skin protection, astringency, opacity, etc.); skin conditioning agents; solvents (liquids employed to dissolve components found useful in the cosmetics or drugs); and surfactants (as cleansing agents, emulsifying agents, solubilizing agents, and suspending agents).

Figure 2A:
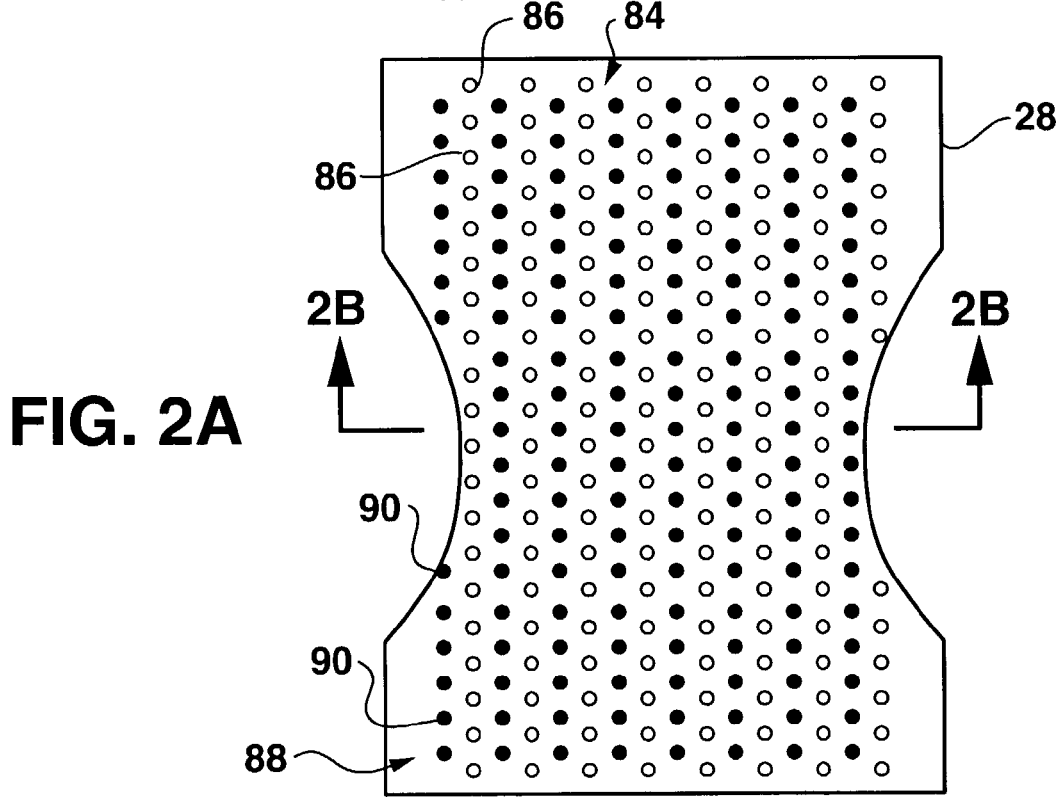
FIG. 2A is a planar view of an embodiment of a body facing liner incorporating phase-change lotion and liquid deposits according to the invention.

The lotion formulation deposits may be applied in a matrix or pattern to the entire bodyfacing surface of the liner 28, as shown in FIG. 2A, or may be selectively applied to particular sections of the liner 28, such as the medial section along the longitudinal centerline of the diaper, to provide greater lubricity of such sections and to transfer such lotion to the wearer's skin. The lotion formulation should cover a sufficient amount of the surface area of the bodyside surface of the liner 28 to ensure adequate transfer to the skin and reduced abrasion between the liner 28 and the wearer's skin.

The lotion formulation can be applied to the bodyside liner 28 at any add-on level which provides the desired transfer benefit. For example, the total add-on level of the lotion formulation can be from about 0.05 to about 100 mg/cm$^2$, desirably from about 1 to about 50 mg/cm$^2$ and more desirably from about 10 to about 40 mg/cm$^2$ for improved performance. The add-on amount will depend upon the desired effect of the lotion on the product attributes and the specific lotion formulation.

The lotion formulation may be applied to the bodyside liner 28 in any of many well known manners. For example, the phase-change lotion may be deposited by use of a piezo-driven print head. The piezo-driven print devices are typically capable of emitting droplets having a diameter in the range of about 50–90 micrometers with placement resolution to about 1/200 of an inch. The phase-change liquid may be deposited in a single or multiple pass of the top cover 12 past the print head. In an alternate desirable embodiment, the phase-change liquid is deposited by an inkjet printing technique. Suitable inkjet printing techniques are described, for example, in co-pending U.S. patent application Ser. No. 09/990,686 filed on Nov. 16, 2001, and entitled "MATERIAL HAVING ONE OR MORE CHEMISTRIES WHICH PRODUCE TOPOGRAPHY, UNIQUE FLUID HANDLING PROPERTIES AND/OR BONDING PROPERTIES THEREON AND/OR THEREIN" and U.S. patent application Ser. No. 09/991,185 filed on Nov. 16, 2001, and entitled "APPARATUS AND METHOD TO PRODUCE TOPOGRAPHY, UNIQUE FLUID HANDLING PROPERTIES AND BONDING PROPERTIES ON OR WITHIN SUBSTRATES." These co-pending applications are incorporated herein by reference for all purposes.

For example, the lotion formulation may be applied to the bodyside liner 28 by (a) heating the lotion formulation to a temperature above the melting point of the formulation, causing the formulation to melt, (b) applying the melted formulation to the bodyfacing surface of the liner 28 in the desired matrix of discrete deposits; and (c) resolidifying the deposits of the melted formulation. Desirably, resolidification of the deposits occurs almost instantaneously, without the need for external cooling means such as chill rolls. This can occur if the formulation is heated to a temperature only slightly above or at the melting point of the formulation. However, external means such as chill rolls, either before or after the application of melt, can be used if desired to accelerate resolidification. The increased viscosity of the lotion at the process temperature and the instantaneous resolidification tends to impede penetration of the formulation into the liner 28 and absorbent body 32 of the article and retain it on the bodyfacing surface of the liner 28, which is advantageous.

The article 100 also includes discrete deposits of a second type of phase-change liquid having a melting point greater than body temperature. These deposits define a topography or height above the bodyfacing surface of the liner 28 sufficient to maintain the liner 28 spaced from the wearer's skin to reduce irritation and abrasion caused by the liner 28 rubbing against the skin. The second phase-change liquid may or may not have a skin wellness component. For example, the second phase-change liquid may be similar to the phase-change lotion formulation with the exception that the wax has a higher melting point in the second phase-change liquid. Alternatively, the second phase-change liquid may be formed entirely of a wax. The second phase-change liquid should be selected to ensure that it sufficiently adheres to the liner 28. Exemplary phase-change liquids include, but are not limited to, waxes, petrolatum based materials, adhesives, thermoplastics, and generally any skin-friendly material that can be applied to the liner in a molten state and which subsequently solidifies into discrete deposits.

The second phase-change liquid may be applied to the liner 28 by any manner or technique as discussed above with respect to the skin wellness lotion formulation.

In a particular embodiment as illustrated in FIG. 2A, a first matrix or pattern 84 of discrete deposits 86 of the skin wellness lotion formulation are applied directly onto the body facing surface of the liner 28. As discussed, the phase-change lotion formulation has a phased change temperature that is less than body temperature. The discrete deposits 84 may be applied in any pattern or matrix. In the illustrated embodiment of FIG. 2A, the deposits 84 are defined as rows of dots or dome-like structures. The structures may have a radius within the range of about 0.005 mm to about 3.0 mm, and a height h1 (FIG. 2B) above the body facing surface of the liner 28 that is generally about equal to the radius of the structures. The density of deposits 84 (number per surface area of liner 28) may be empirically determines so as not to inhibit the ability of the liner 28 to intake fluids for absorption by the underlying absorbent structure 32. In this regard, it may generally not be preferred to coat or uniformly spray the body side liner 28 with the skin wellness lotion formulation.

Figure 2B:
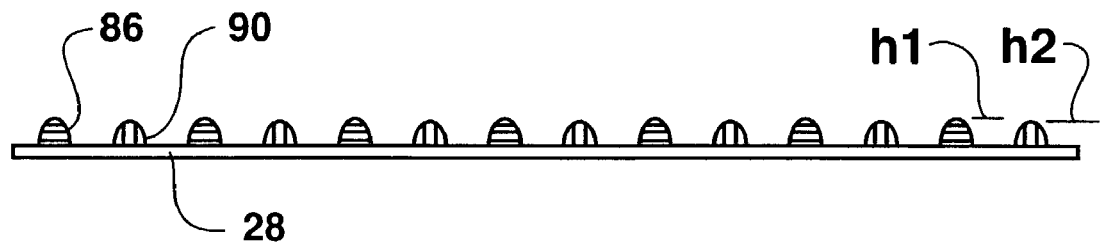
FIG. 2B is a cross-sectional view of the liner of FIG. 2A taken along the lines indicated.

Referring to FIG. 2B, it can be seen that the lotion formulation deposits 86 have a topography or height h1 so that the deposits 86 will directly contact the wearer's skin and, upon melting, the lotion formulation will be transferred to the wearer.

Still referring to FIG. 2A, the liner 28 also includes a second matrix 88 of the discrete deposits 90 of a phase-change liquid applied to the body facing surface of the liner. The deposits 88 are interspaced with the deposits 84 of the lotion formulation and have a height h2 above the liner surface less than the height h1 of the lotion deposits 84. The deposits 90 have a phase-change temperature greater than body temperature and serve primarily to maintain the liner 28 spaced from the wearer's skin. As with the lotion deposits 84, in this particular embodiment, the phase-change liquid deposits 90 are defined as a lines of individual dome-like structures.

It should be appreciated that the size of deposits 84 and 90 are greatly exaggerated in the drawings for sake of illustration purposes.

Figure 4:
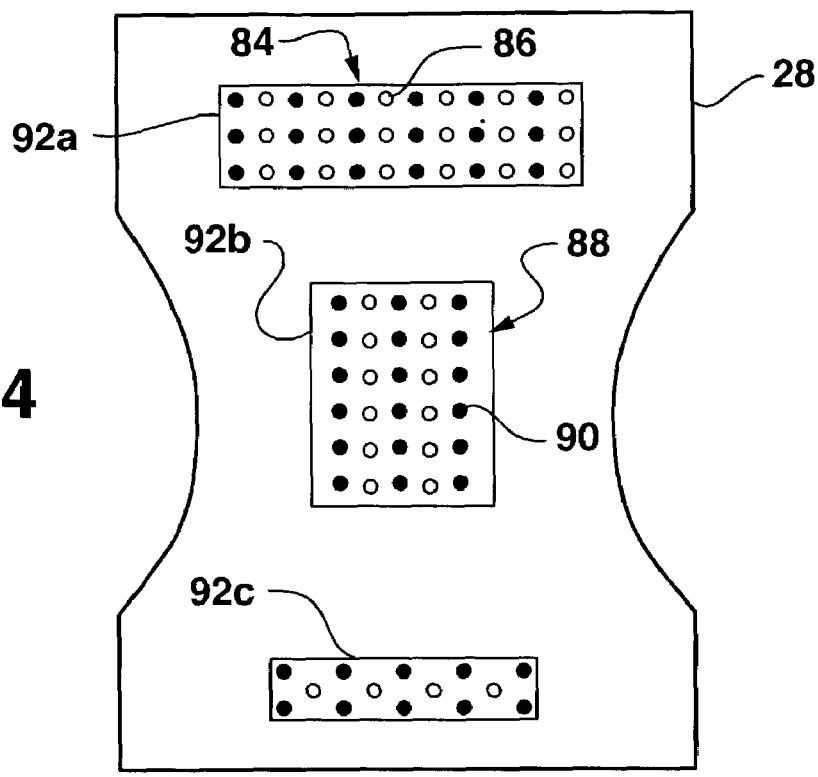
FIG. 4 is an alternative view of an embodiment of a liner according to the invention.

The embodiment of FIG. 2A depicts the deposits 86 and 90 as applied generally in a pattern over the entirety of the liner 28. In an alternate embodiment, for example as illustrated in FIG. 4, the deposits 86 and 90 may be defined only in select regions or portions of the liner, such as regions 92a, 92b, and 92c. It may be desired to target only specific regions of the liner that are more prone to cause irritation or discomfort to the wearer.

Figure 3:
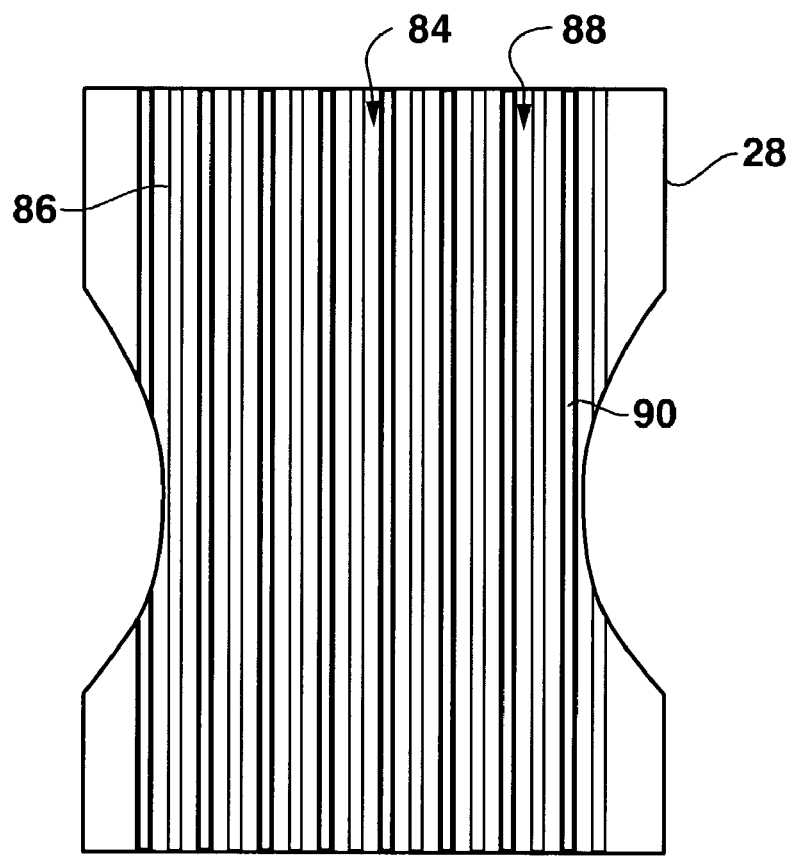
FIG. 3 is a planar view of an alternative embodiment of a liner according to the invention.

In the embodiment illustrated in FIG. 3, the liner 28 includes a first matrix 84 of lotion formulation deposits 86 defined as generally continuous lines along the liner 28. Likewise, the matrix 88 of the phase-change liquid deposits 90 are also defined as generally continuous lines. The deposit lines 86 and 90 may alternate.

It should be appreciated that the matrix 84 of lotion deposits 86 may be defined in a first pattern, such as dome-like structures or lines, and the matrix 88 of phase-change liquid deposits 90 may be defined as a different matrix or pattern.

Figure 5:
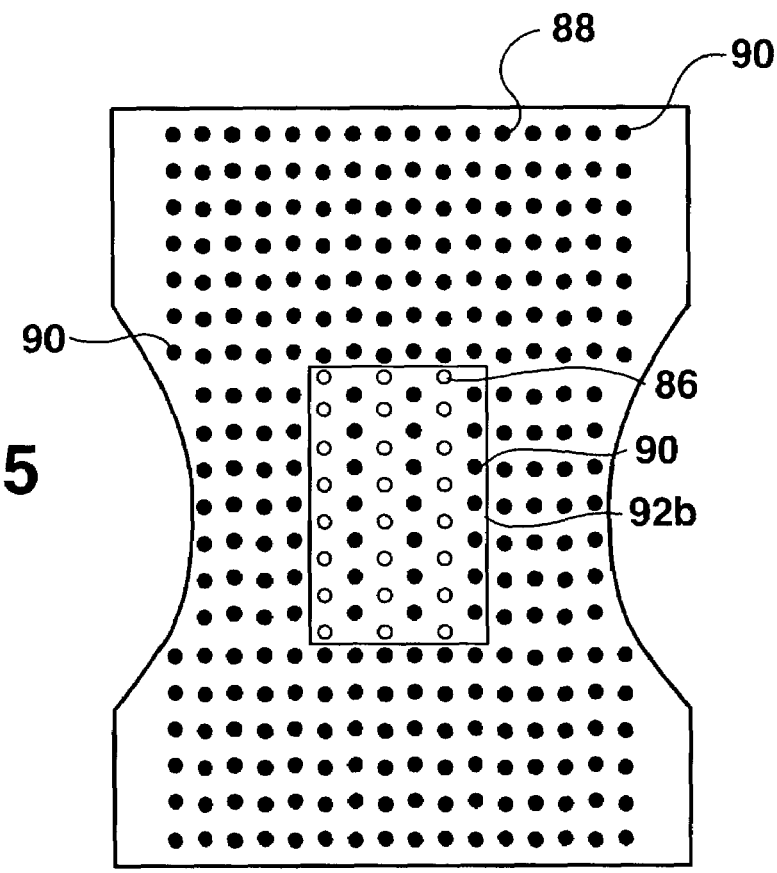
FIG. 5 is an alternative view of an embodiment of a liner according to the invention.

FIG. 5 illustrates an embodiment wherein a central portion or region 92b of the liner incorporates the skin wellness lotion deposits 86 as well as the phase change liquid deposits 90. The remaining regions of the liner 28 have only the phase-change liquid deposits 90 defined thereon. This particular embodiment may be desired in that it maintains the entirety of the liner 28 displaced from the wearer's skin yet applies the lotion formulation only to selected areas.

Figure 6A:
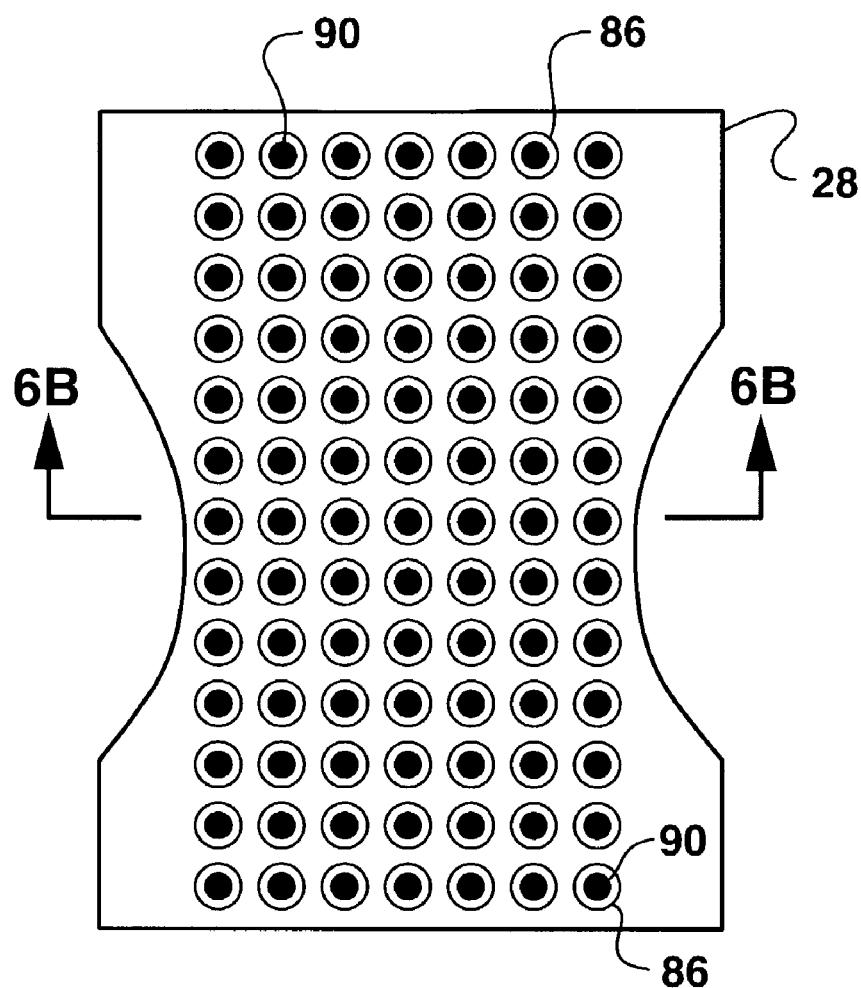
FIG. 6A is an alternative view of an embodiment of a liner according to the invention.
Figure 6B:
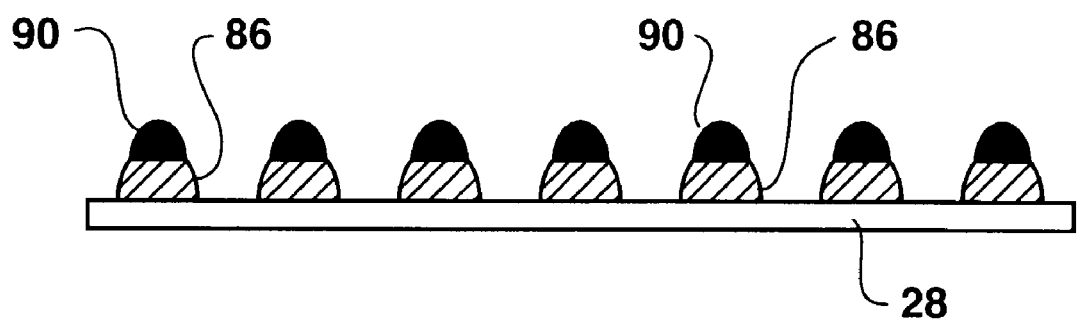
FIG. 6B is a cross-sectional view of the embodiment of FIG. 6A taken along the lines indicated.

It is not necessary that the lotion formulation deposits 90 be applied directly to the body facing surface of the liner 28. The deposits 90 may be applied at any relative location with respect to the liner 28 so as to contact the wearer's skin for transferring lotion thereto. For example, in the embodiment of FIGS. 6A and 6B, the lotion deposits 90 are formed on top of the phase change liquid deposits 86. This configuration may be formed, for example, in multiple passes of the liner substrate under the same print head, or passing the liner 28 under a first print head to deposit the phase-change liquid deposits 90, and then under a downstream print head to apply the deposits 86 of lotion formulation on top of the deposits 90. Referring to FIG. 6B, it can be readily seen that in use of the article, the deposits 86 will contact the wearer's skin and, upon being melted, the lotion formulation will be transferred to the wearer's skin. Once the deposits 86 are depleted, the phase-change liquid deposits 90 will contact the wearer's skin and maintain the liner 28 displaced from the skin.

It should be understood that resort may be had to various other embodiments, modifications, and equivalents to the embodiments of the invention described herein which, after reading the description of the invention herein, may suggest themselves to those skilled in the art without departing from the scope and spirit of the present invention.

What is claimed is:

1. An absorbent article, comprising:
    an outer cover member;
    a liner defining a bodyfacing surface, said liner disposed over said cover member;
    an absorbent body structure disposed between said outer cover member and said liner;
    a first matrix of discrete deposits of a first phase-change skin wellness lotion formulation applied to said bodyfacing surface of said liner, said first phase-change lotion formulation having a phase-change temperature less than body temperature;
    a second matrix of discrete deposits of a second phase-change liquid applied to said bodyfacing surface of said liner interspaced with said deposits of first phase-change lotion deposits, said second phase-change liquid deposits having a phase-change temperature greater than body temperature; and
    wherein said first phase-change lotion deposits have a height above said bodyfacing surface greater than a height of said second phase-change liquid deposits.

2. The absorbent article as in claim 1, wherein said matrix of first phase-change lotion deposits comprises discrete droplets forming dome-like structures on said bodyfacing surface.

3. The absorbent article as in claim 2, wherein said dome-like structures have a radius of between about 0.005 mm and about 3.0 mm, and a height above said bodyfacing surface about equal to said radius.

4. The absorbent article as in claim 1, wherein said matrix of second phase-change liquid deposits comprises discrete droplets forming dome-like structures on said bodyfacing surface.

5. The absorbent article as in claim 4, wherein said dome-like structures have a radius of between about 0.005 mm and about 3.0 mm, and a height above said bodyfacing surface about equal to said radius.

6. The absorbent article as in claim 1, wherein said matrix of first phase-change lotion deposits and matrix of second phase-change liquid deposits comprise discrete droplets forming dome-like structures on said bodyfacing structure.

7. The absorbent article as in claim 1, wherein said deposits of first phase-change lotion and said second phase-change liquid are applied generally uniformly over an entirety of said bodyfacing surface of said liner.

8. The absorbent article as in claim 1, wherein said deposits of first phase-change lotion and said second phase-change liquids are applied to discrete areas of said bodyfacing surface.

9. The absorbent article as in claim 1, wherein said first phase-change lotion comprises an emollient.

10. The absorbent article as in claim 9, wherein said emollient is selected from the group consisting of oils, esters, glycerol esters, ethers, alkoxylated carboxylic acids, alkoxylated alcohols, fatty alcohols, and mixtures thereof.

11. The absorbent article as in claim 9, wherein said emollient is a petroleum based emollient.

12. The absorbent article as in claim 1, wherein said first phase-change lotion comprises a wax.

13. The absorbent article as in claim 12, wherein wax is selected from the group consisting of animal based waxes, vegetable based waxes, mineral based waxes, silicone based waxes, and mixtures thereof.

14. The absorbent article as in claim 1, wherein said first phase-change lotion comprises a combination of a wax, an emollient, and a viscosity enhancer.

15. The absorbent article as in claim 1, wherein said second phase-change liquid is selected from the group consisting of a wax, petroleum based product, thermoplastic, adhesive, and combinations thereof.

16. The absorbent article as in claim 1, wherein said first phase-change lotion comprises a wax having a melting point below body temperature, and said second phase-change liquid comprises a wax having a melting point above body temperature.

17. The absorbent article as in claim 1, wherein said first phase-change lotion deposits and said second phase-change liquid deposits are applied to said bodyfacing surface in alternating lines.

18. The absorbent article as in claim 17, wherein said lines are applied by an inkjet printing process.

19. The absorbent article as in claim 17, wherein said lines are generally continuous.

20. The absorbent article as in claim 17, wherein said lines are broken.

21. The absorbent article as in claim 20, wherein said lines comprise lines of discrete droplets.

22. An absorbent article, comprising:
    an outer cover member;
    a liner defining a bodyfacing surface, said liner disposed over said cover member;
    an absorbent body structure disposed between said outer cover member and said liner;
    a matrix of discrete deposits of a phase-change liquid applied to said bodyfacing surface of said liner, said phase-change liquid deposits having a height with respect to said bodyfacing surface so as to maintain said bodyfacing surface away from a wearer's skin in use of said article, said phase-change liquid deposits having a melting temperature greater than body temperature;
    a matrix of discrete deposits of a phase-change skin wellness lotion formulation applied relative to said bodyfacing surface of said liner so as to extend above said phase-change liquid deposits, said phase-change lotion deposits having a phase-change temperature less than body temperature;
    and wherein in use of said article, said deposits of phase-change lotion formulation contact a wearer's skin and transfer said lotion formulation to the wearer's skin, and said deposits of said phase-change liquid contact the wearer's skin and maintain said liner away from the skin upon said phase-change lotion deposits being reduced in height to below the height of said phase-change liquid deposits.

23. The absorbent article as in claim 22, wherein said skin wellness lotion deposits are applied directly to said bodyfacing surface of said liner interspaced with said phase-change liquid deposits.

24. The absorbent article as in claim 23, wherein said skin wellness lotion deposits and said phase-change liquid deposits comprise discrete droplets forming dome-like structures on said bodyfacing structure.

25. The absorbent article as in claim 22, wherein said skin wellness lotion deposits are applied on top of said phase-change liquid deposits.

26. The absorbent article as in claim 22, wherein said skin wellness lotion formulation comprises an emollient.

27. The absorbent article as in claim 26, wherein said emollient is selected from the group consisting of oils, esters, glycerol esters, ethers, alkoxylated carboxylic acids, alkoxylated alcohols, fatty alcohols, and mixtures thereof.

28. The absorbent article as in claim 26 wherein said emollient is a petroleum based emollient.

29. The absorbent article as in claim 22, wherein said skin wellness lotion formulation comprises a wax.

30. The absorbent article as in claim 29, wherein said wax is selected from the group consisting of animal based waxes, vegetable based waxes, mineral based waxes, silicone based waxes, and mixtures thereof.

31. The absorbent article as in claim 22, wherein said skin wellness formulation comprises a combination of a wax, an emollient, and a viscosity enhancer.

32. The absorbent article as in claim 22, wherein said phase-change liquid is selected from the group consisting of a wax, petroleum based product, thermoplastic, adhesive, and combinations thereof.

* * * * *